US006945121B2

(12) United States Patent
Honer et al.

(10) Patent No.: US 6,945,121 B2
(45) Date of Patent: Sep. 20, 2005

(54) APPARATUS FOR SIMULATING A DYNAMIC FORCE RESPONSE

(75) Inventors: Peter D. Honer, Neenah, WI (US); Oliver P. Renier, Green Bay, WI (US); Peter S. Lortscher, Neenah, WI (US)

(73) Assignee: Kimberly, Clark Worldwide, Inc., Neenah, WI (US)

( * ) Notice: Subject to any disclaimer, the term of this patent is extended or adjusted under 35 U.S.C. 154(b) by 238 days.

(21) Appl. No.: 10/309,836

(22) Filed: Dec. 4, 2002

(65) Prior Publication Data

US 2004/0107776 A1 Jun. 10, 2004

(51) Int. Cl.$^7$ ................................................. G01N 3/00
(52) U.S. Cl. ............................................................ 73/760
(58) Field of Search ........................... 73/760, 800, 801, 73/802, 803, 804, 805

(56) References Cited

U.S. PATENT DOCUMENTS 3,026,724 A    3/1962   Gstaldar
3,763,698 A   10/1973   Suzuki et al.
5,654,500 A    8/1997   Herron et al.

FOREIGN PATENT DOCUMENTS

FR    1437945    5/1966
GB    1464682    2/1977

OTHER PUBLICATIONS

International Search Report PCT/US 03/26342, dated May 28, 2004, 4 pages.

Primary Examiner—Max Noori
Assistant Examiner—Alandra Ellington
(74) Attorney, Agent, or Firm—Senniger, Powers, Leavitt & Roedel

(57) ABSTRACT

Apparatus for generating a dynamic force response that simulates a dynamic force typically generated by an experimental event. A cam having a profile, such as a serrated profile, rotates about an axis according to a rotational speed profile. A braking device operatively connects to the cam, such as a follower biased against the cam, for generating a braking force resisting rotation of the cam. A measurement device measures the braking force on the cam to generate the dynamic force response.

35 Claims, 8 Drawing Sheets

APPARATUS FOR SIMULATING A DYNAMIC FORCE RESPONSE

BACKGROUND OF THE INVENTION

This invention relates to dynamic force testing machines, and more particularly to an apparatus for simulating a dynamic force response corresponding to an experimental event, such as a peel test for an adhesive-backed substrate or refastenable system (e.g., a hook-and-loop fastener system).

Dynamic force testing machines, such as tensile testing machines (i.e., constant speed of extension machines), commonly perform experiments to measure particular characteristics of materials or objects. These measured characteristics may then be used for further evaluation of the materials or objects. For example, materials may be dynamically tested on tensile testing machines to ascertain their mechanical properties. Such tests are typically performed with multiple samples of different materials, creating a library of measured test data comparing different materials to one another. For such libraries of data to be useful, consistent performance by the testing machine is essential. This is particularly true for dynamic testing machines, where multiple measurements (e.g., force, extension displacement) are recorded over time, generating a dynamic response of a particular characteristic, such as force.

One such experiment is a peel test for a hook-and-loop fastener. When the mating components of a hook-and-loop fastener are peeled apart, the force required to disengage the hooks from the loops varies over time. As graphically depicted, this force typically has a sawtooth or serrated profile that varies over time, caused by gradual increases in the peeling force as individual hooks are plastically deformed, followed by momentary drops in force as the hooks release from respective loops. Consistently reproducing such a sawtooth dynamic force response, or any such dynamic force response, is the focus of the present invention.

Conventional testing machines (e.g., tensile testing machines) performing dynamic testing have suffered from various drawbacks, most notably the inability to calibrate the testing machines to ensure consistent dynamic testing. For instance, performing multiple tests on similar portions of material may yield variability between tests. However, determining whether such variability stems from the testing machine or the material itself, is difficult if not impossible. To minimize variability in the testing machines, those skilled in the art utilize calibration methods. As used herein, 'calibration' denotes verification of a machine's accuracy, usually with an accompanying adjustment of the machine to minimize its error. Typical calibration techniques are static. 'Static calibration' denotes calibration of a machine where the test specimen or moving elements of the machine are either fixed or change position slowly, such that dynamic effects upon the machine are negligible. Because dynamic effects are not included in the calibration, static calibration techniques cannot accurately calibrate the dynamic response of a particular machine. A machine calibrated statically, yet performing dynamic-tests, may or may not be performing accurately. As such, dynamic calibration techniques may be used to better confirm the dynamic performance of a machine. 'Dynamic calibration' denotes calibration of a machine where the test specimen or moving elements of the machine change position quickly, such that dynamic effects upon the machine are no longer negligible. Dynamic calibration is useful when applied to a single measured characteristic, or channel (e.g., force, displacement, time), of the testing machine by itself. Beyond dynamic calibration of a single channel by itself, however, dynamic calibration may be more effectively applied to multiple channels simultaneously. Such a multi-channel calibration not only dynamically calibrates the individual channels, it dynamically calibrates their interaction with one another. Without such simultaneous calibration of such channels, individual calibration of each channel separately cannot account for potential changes occurring only when such characteristics are measured simultaneously.

Specifically, conventional static calibration techniques used in conjunction with tensile testing machines involve only static calibration of the force sensing portions of the tensile testing machines, including load cells and any associated recording circuitry of the machines. By moving elements of the tensile testing machine (e.g., extending a crossbar) slowly during the static calibration, the actual dynamic movement of the tensile testing machine, as compared to the desired dynamic movement, is not calibrated. Actual movements of the tensile testing machine must accurately match the desired movements of the machine, however, because movements of the machine are often incorporated into other measured characteristics. For example, tensile testing machines may be used to create a force versus extension curve. Because static calibration only calibrates the ability of the tensile testing machine to measure a single characteristic or channel (e.g., force, displacement), in a static condition, the measurements reported by the tensile testing machine when both characteristics are measured simultaneously may be inaccurate, casting doubt over the accuracy of the curve. Limiting the calibration to only static or dynamic calibration of individual characteristics by themselves does not sufficiently calibrate the machine for a dynamic test. For instance, many material properties are strain and strain-rate dependent, making extension displacement an important characteristic that should be calibrated simultaneously with force to ensure accuracy. Various ASTM standards specify accuracy requirements for tensile testing machine measurements. The widely accepted ASTM E4 calibration procedure, for example, employs deadweights or highly accurate load cells to calibrate only the force measurement and recording system of the tensile testing machine. Because no other portion of the tensile testing machine is calibrated, however, this process yields only a static calibration of a single characteristic and cannot gauge the true dynamic response of the tensile testing machine. Furthermore, many conventional tensile testing machine software programs have user selectable or configurable sampling rates and data filters for dynamic testing. Mere deadweight calibration of such machines does not ensure that the machine is operating properly for a given dynamic test. In other words, applying conventional calibration methods to dynamic tensile testing machines calibrates only particular individual characteristics of the machine separately from one another, whereas simultaneous dynamic calibration occurs while the machine performs dynamically, thereby calibrating all parts of the machine and measured characteristics together (e.g., load cell and extension together). Applying such a calibration verifies the interaction of individual measured characteristics with one another.

There is a need, therefore, for an apparatus and method capable of accurately dynamically calibrating the various measurement channels of a tensile testing machine, or any testing machine, simultaneously by performing repeatable dynamic testing simulating actual experimental events, such as (but not limited to) the aforementioned peel tests. For instance, such an apparatus and method would dynamically calibrate two or more measurements simultaneously during a simulated dynamic test to verify the accuracy of such measurements when measured together simultaneously. For additional detail regarding methods for simulating a dynamic force response and methods of calibration, reference may be made to the utility application filed simultaneously by Peter D. Honer, Oliver P. Renier and Peter S. Lortscher, entitled METHOD FOR SIMULATING A DYNAMIC FORCE RESPONSE AND METHOD OF CALIBRATION, assigned to Kimberly-Clark Worldwide, Inc., the entire disclosure of which is incorporated by reference in a manner consistent herewith.

BRIEF SUMMARY OF THE INVENTION

In general, apparatus of the present invention simulates a dynamic force event in a force testing machine having a force measurement device. The apparatus comprises a cam rotatable about an axis according to a rotational speed profile. A braking device operatively connects to the cam for generating a braking force resisting rotation of the cam. A mechanism connects the cam to the force measurement device whereby the force measurement device is adapted to measure the braking force on the cam as the cam rotates according to the rotational speed profile.

In another aspect of the invention, apparatus of the present invention comprises a first body and a second body biased into contact with a surface on the first body to impart a braking force against the surface. The first and second bodies are movable relative to one another according to a specified speed profile. A measurement device operatively connects to the first body to measure the braking force on the first body as the bodies move relative to one another according to a speed profile. The braking force varies according to the friction between the surface and the second body moving against one another.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION OF THE PREFERRED EMBODIMENTS

Figure 1:
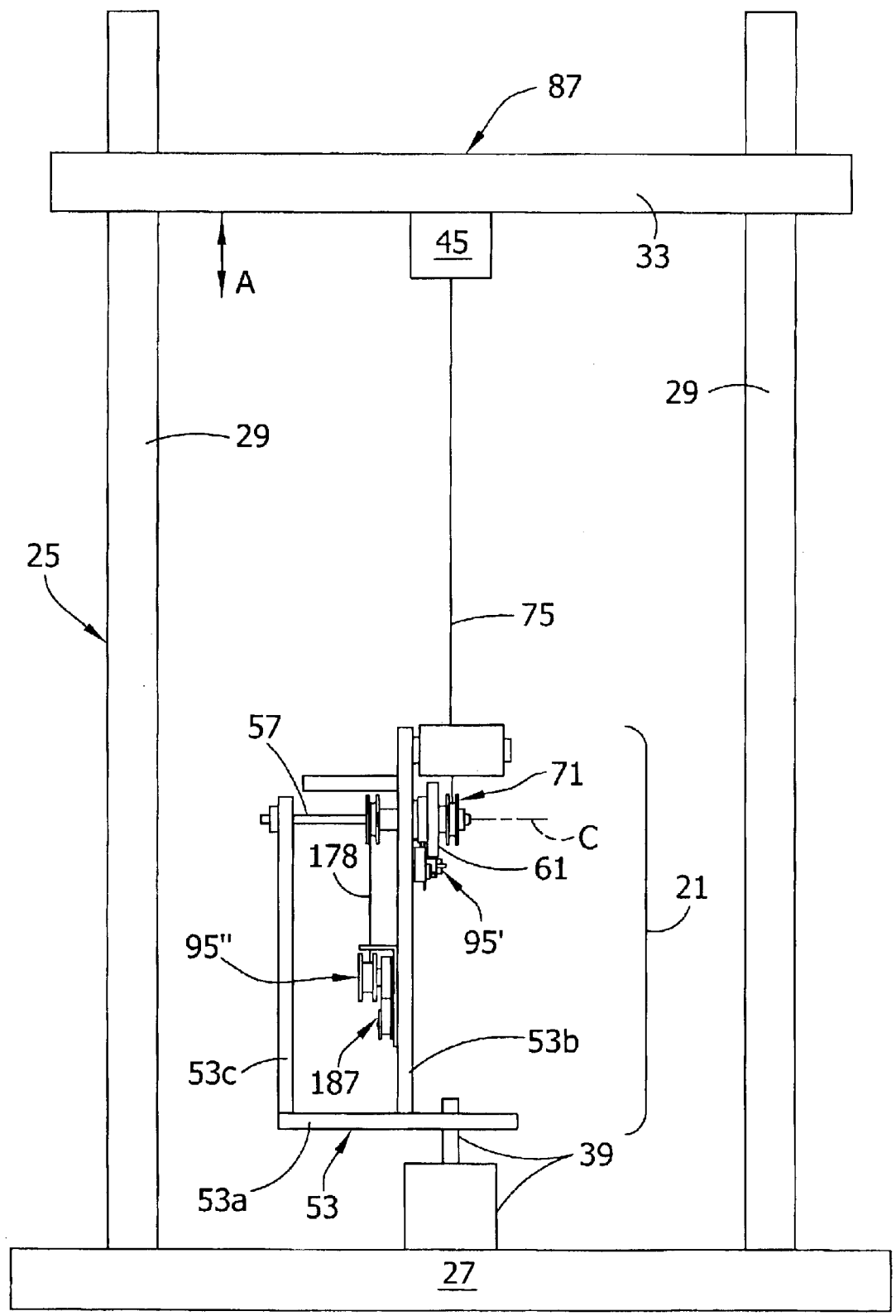
FIG. 1 is a front elevation of a tensile testing machine and an apparatus of the present invention for simulating and measuring a dynamic force.

Referring to FIG. 1, apparatus of this invention for simulating a dynamic force over time corresponding to an experimental event is designated 21 in its entirety. In one embodiment, the apparatus 21 mounts on a tensile testing machine, generally designated 25, having a base 27, two uprights 29 extending up from the base 27 and a crossbar 33 extending between the uprights above the base 27. The crossbar 33 is movable by a conventional mechanism along the uprights 29 in the directions of arrow A. The construction and operation of such a tensile testing machine 25 is well known in the art and will not be described here. The apparatus 21 mounts on the base 27 of the tensile testing machine 25 via a mount 39 secured to the base. A force measurement device 45 (e.g., a load cell) of the tensile testing machine 25 connects to the apparatus 21 and mounts on the crossbar 33. Other measurement devices, such as strain gages or torque gages, are also contemplated as within the scope of the invention and discussed in greater detail below. The mount 39 and force measurement device 45 are conventional components and will not be described further here. Suffice it to say that the force measurement device 45 mounts on the crossbar 33, such as by conventional mechanical fasteners (not shown), to move along a linear path as the crossbar moves in either of the directions of arrow A (FIG. 1). When used in a conventional manner to conduct a peel test for a test specimen, such as a hook-and-loop fastener, the tensile testing machine 25 would appear essentially as shown in FIG. 1, except that the apparatus 21 would be replaced by the test specimen to be tested.

Figure 2:
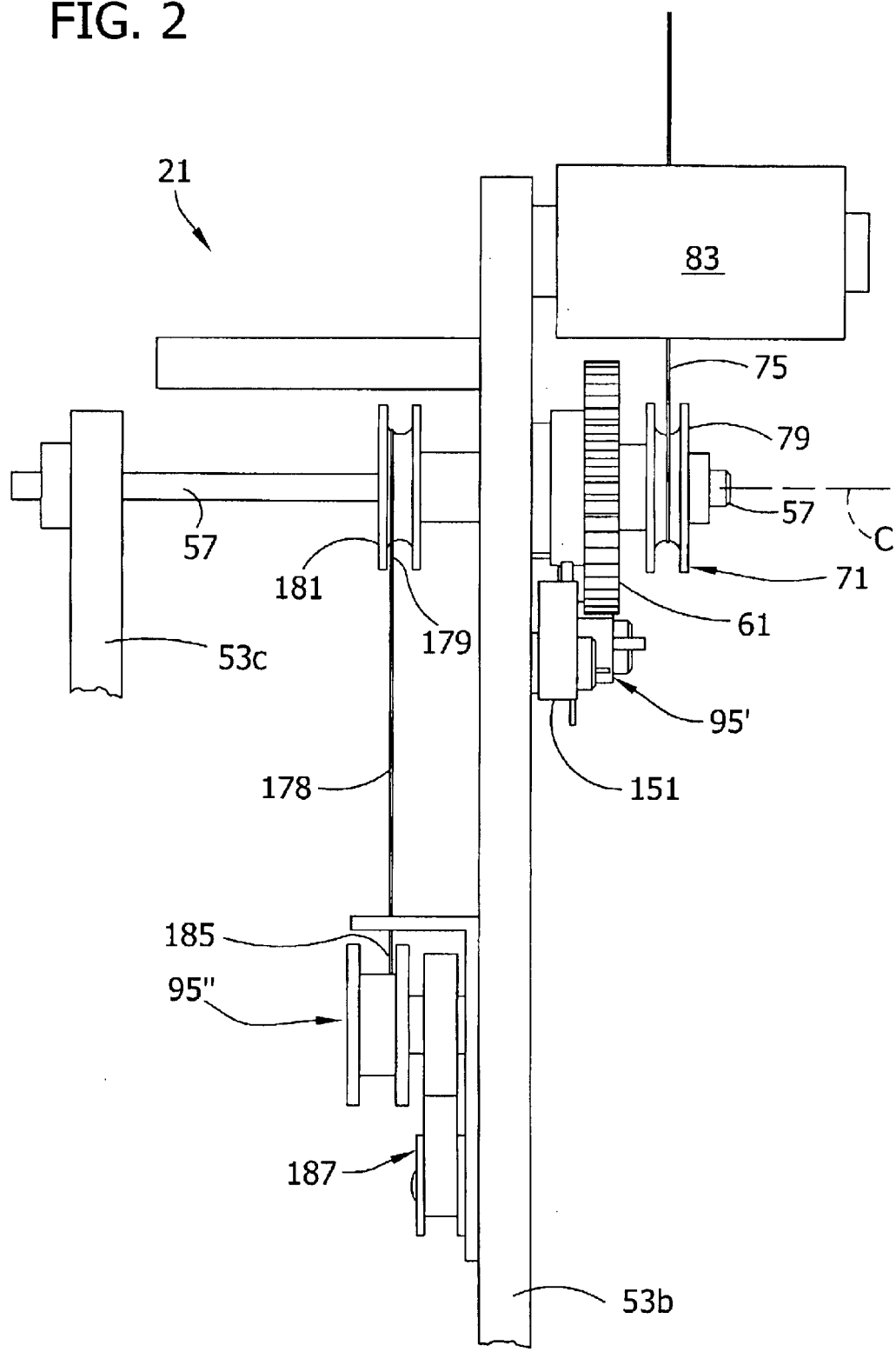
FIG. 2 is an enlarged portion of the apparatus of FIG. 1.

The focus of the present invention is the apparatus 21, which is depicted in greater detail in FIGS. 2–5. The apparatus 21 comprises a bracket 53 for mounting the elements of the apparatus. The bracket 53 has three portions, a horizontal plate 53a secured to the mount 39, a primary support 53b extending up from the plate and a secondary support 53c extending up from the plate generally parallel to the primary support (FIGS. 1 and 2). A shaft 57 is rotatably supported by the primary support 53b and the secondary support 53c for rotation about an axis C. A cam 61 is rotatably coupled to the shaft 57 for conjoint rotation with the shaft about axis C. The cam 61 may be attached to the shaft 57 in any number of ways, such as by a set screw, welding, a splined coupling or other suitable mechanism.

In the preferred embodiment, the apparatus 21 includes a drive device comprising a linear-to-rotary drive mechanism, generally indicated at 71, operable to rotate the cam 61 in response to linear movement of the force measurement device 45. The preferred drive mechanism 71 includes a driving cord 75 (a cable, wire or other flexible line) connected at one end to the force measurement device 45 and at its opposite end to a drive pulley 79 rotationally coupled to the cam 61 and shaft 57. A guide roll 83 mounted on a shaft secured to the upper end of support 53b guides the driving cord 75 such that the cord extends upward from the apparatus 21 in a substantially vertical orientation to connect to the force measurement device 45, as shown in FIG. 3.

Referring again to FIG. 1, the tensile testing machine 25 includes a linear drive mechanism, generally indicated 87, adapted for moving the force measurement device 45 along a linear path and actuating the linear-to-rotary drive mechanism 71. In the preferred embodiment, the linear drive mechanism 87 includes the movable crossbar 33 of the tensile testing machine 25, upon which the force measurement device 45 mounts by conventional mechanical fasteners (not shown). Other suitable linear drive mechanisms 87 are also contemplated as within the scope of the present invention. Upon linear movement of the linear drive mechanism 87, the linear-to-rotary drive mechanism 71 rotates the cam 61. More specifically, movement of the crossbar 33 in an upward direction pulls the force measurement device 45 and the driving cord 75 upward, causing the drive pulley 79, shaft 57 and cam 61 to rotate together in the direction of arrow R (FIGS. 3–5). The rate or speed of rotation is predetermined in accordance with a rotational speed profile. In the preferred embodiment, the rotational speed profile provides a substantially constant speed. Such a profile is readily achieved by moving the crossbar 33 of the tensile testing machine 25 upward at a constant speed, such that the driving cord 75 rotates the pulley 79 at a constant angular speed. It is also contemplated within the scope of the invention that a particular test procedure may require that the rotational speed profile vary over time. Such a rotational speed profile may be readily achieved by programming the tensile testing machine 25 to move the crossbar 33 at a speed varying with time or by shaping the pulley 79 to have a shape other than circular, for example.

Figure 3:
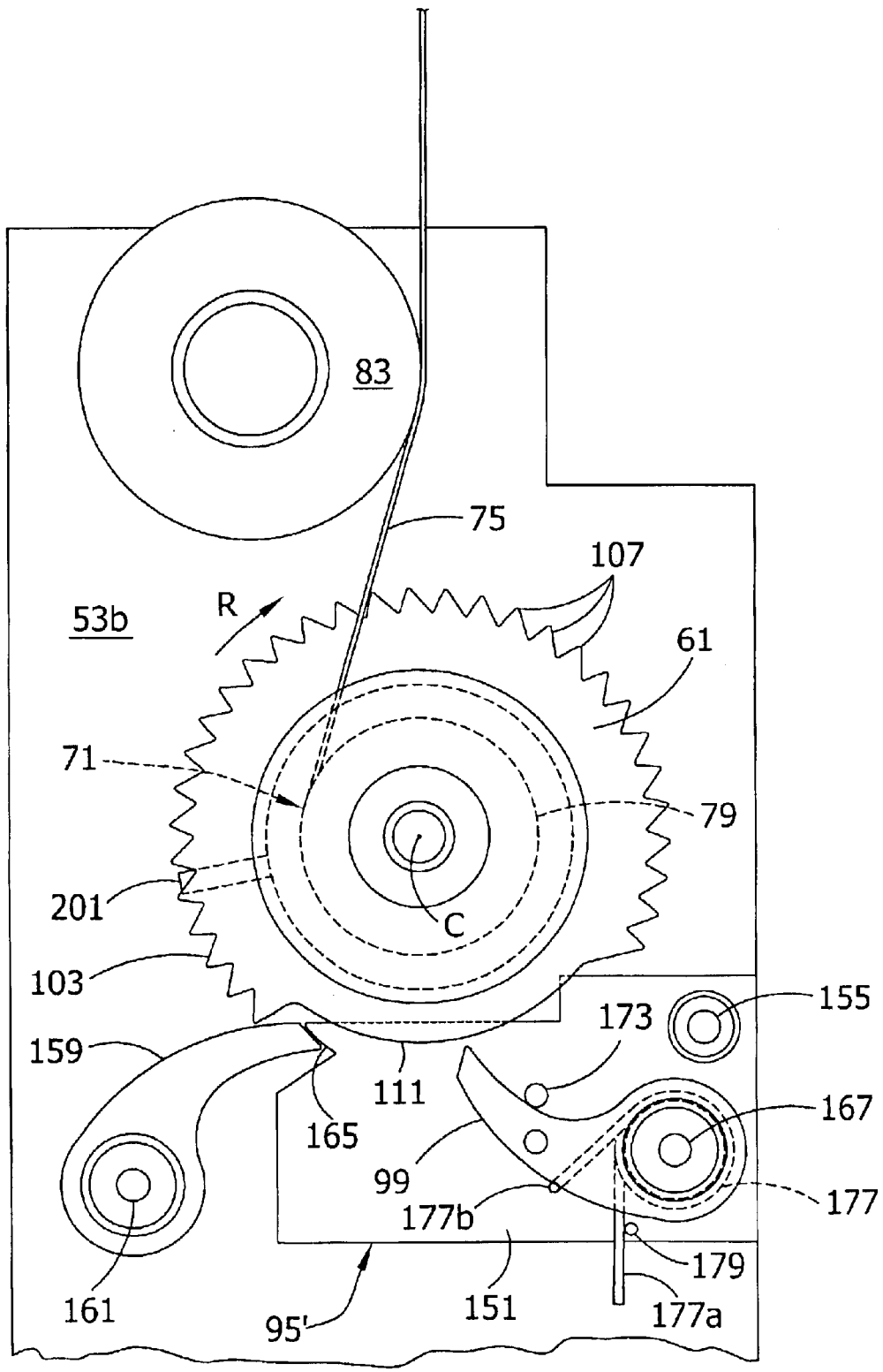
FIG. 3 is a right side elevation of the apparatus of FIG. 2 with a follower positioned for engagement with a cam of the apparatus.
Figure 4:
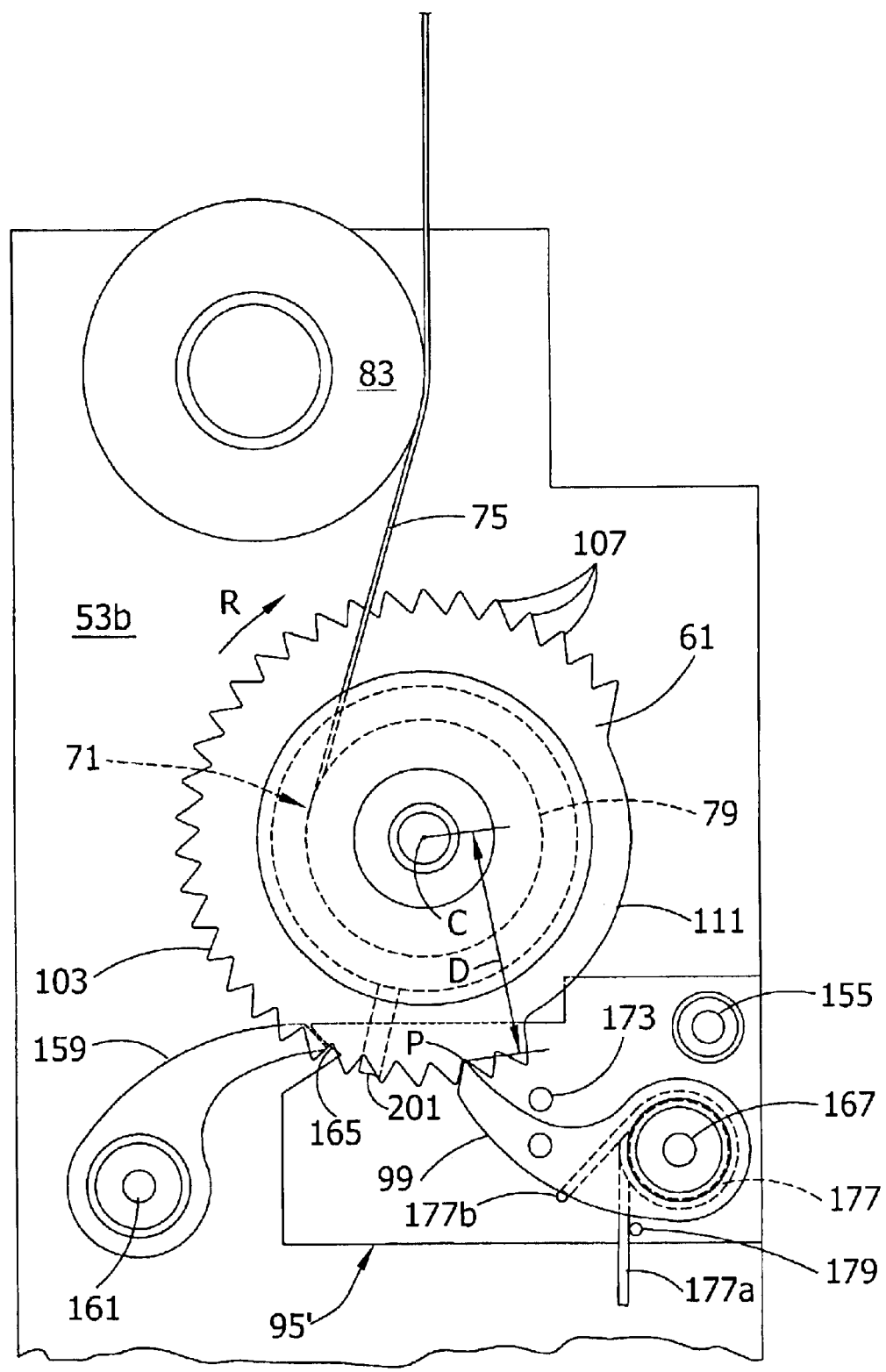
FIG. 4 is a view similar to FIG. 3 showing the follower biased into contact with the cam.
Figure 5:
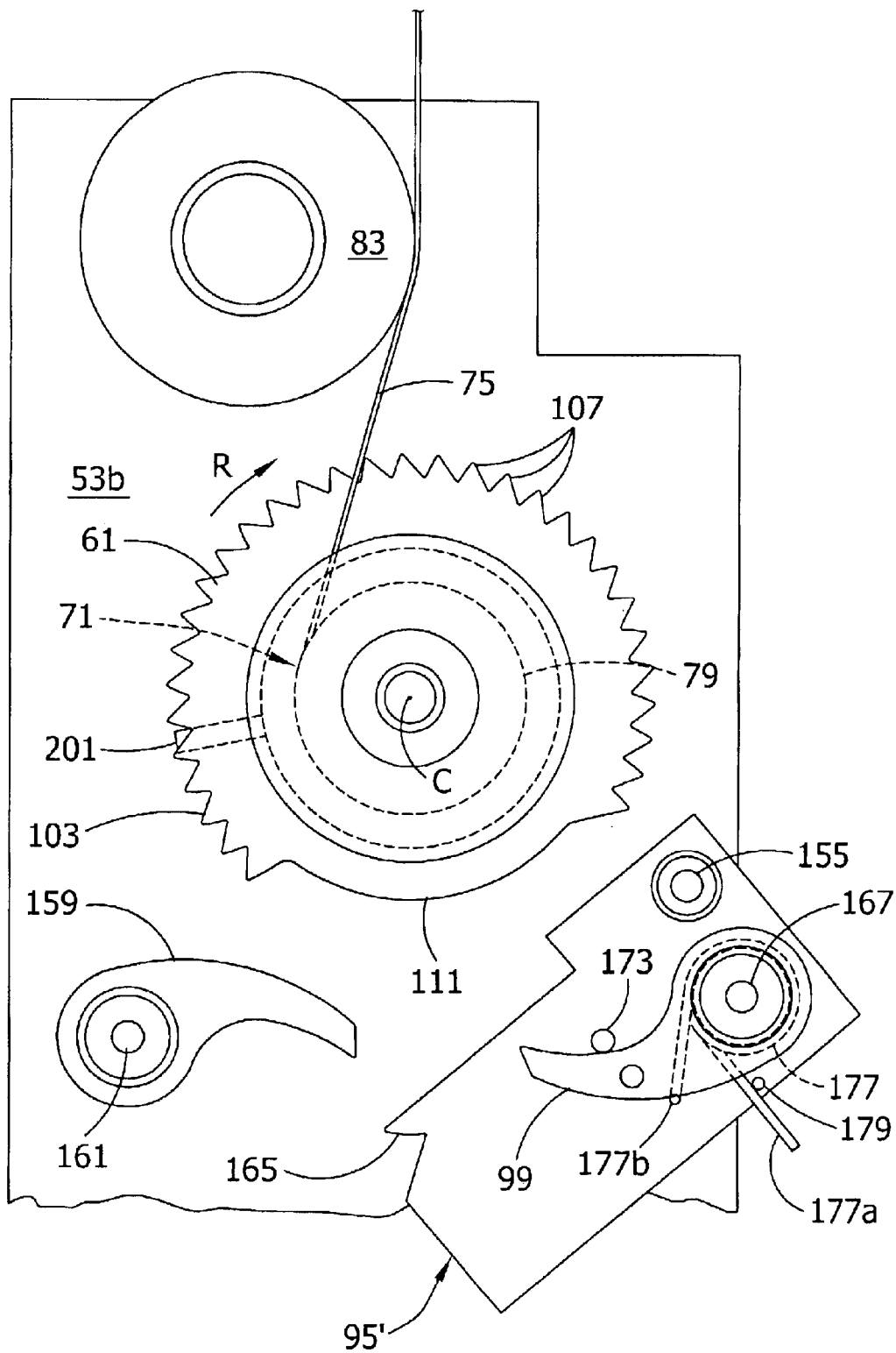
FIG. 5 is a view similar to FIG. 3 showing the follower disengaged from the cam.

The apparatus 21 may further comprise one or more braking devices, generally indicated 95', operatively connected to the cam 61 for generating a braking force, or retrograde force, resisting rotation of the cam (FIGS. 3–5). In one instance, the braking device 95' comprises a follower 99 biased into contact with a surface 103 of the cam 61 and imparting a force against the surface. Friction between the follower 99 and the moving cam 61 creates the braking force resisting cam rotation. The braking force opposing rotation of the cam 61 varies according to the friction between the cam surface 103 and the follower 99 and the normal force component of the follower on the cam. As will be described in greater detail below, the normal force component varies according to the shape of the cam 61. Other braking devices 95' are also contemplated as within the scope of the present invention, such as magnetic, electromagnetic or electrostatic brakes.

Figure 7:
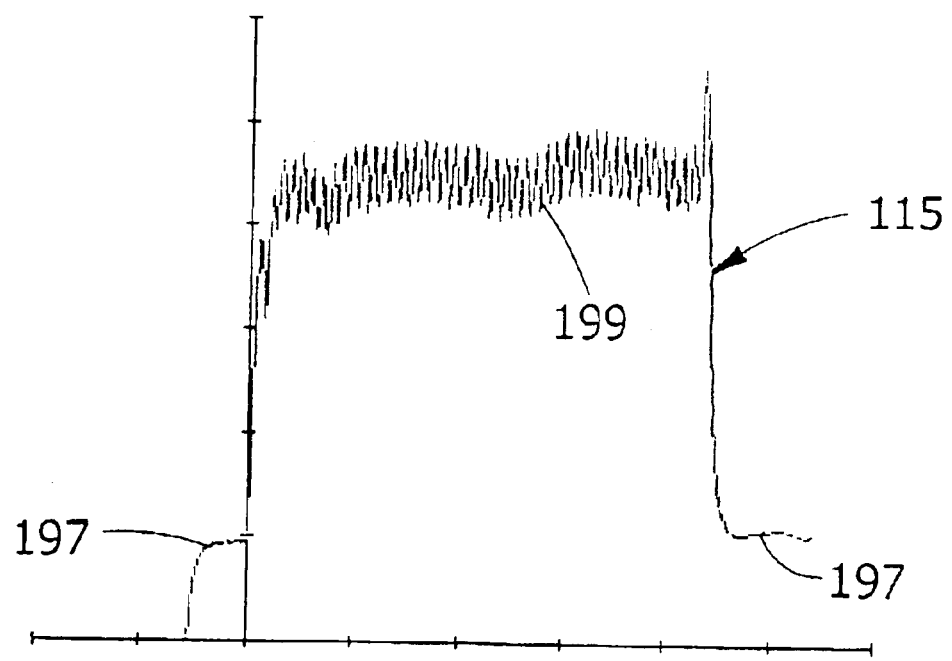
FIG. 7 is a plot of a simulated dynamic force response, wherein the x-axis represents extension and the y-axis represents force.

The cam surface 103 of the braking device 95' is shaped to vary the braking force exerted by the follower 99 over time to simulate the desired dynamic force event. In one embodiment, the cam surface 103 includes a segment having teeth 107 and the follower 99 comprises a pawl (also designated 99 for convenience) adapted to contact the teeth. Preferably, the teeth 107 are of uniform size and are evenly spaced along the cam surface 103. Such a cam surface 103 additionally includes a toothless segment 111 sized and shaped to remain free of contact with the pawl 99. The cam surface 103 may be shaped to have other configurations that simulate different dynamic force events, such as the serrated, simulated dynamic force response generally indicated 115 in FIG. 7. A serrated cam surface as shown in the Figures is not always desirable. Depending upon the dynamic force event sought to be simulated, the shape of the cam 61 may be adjusted accordingly. For example, the teeth may be sized and spaced non-uniformly, such that the simulated dynamic force response 115 created by the pawl 99 and the cam surface 103 more closely resembles the locally erratic behavior exhibited in a conventional peel test. The cam surface 103 may also be oriented other than parallel to the rotational axis of the cam 61 (e.g., perpendicular to the rotational axis of the cam).

In the embodiment shown in FIGS. 3–5, the pawl 99 is mounted on a follower support 151 pinned at 155 to the support 53b, the follower support 151 being adapted to pivot between a "follower ready" position shown in FIGS. 3 and 4 in which the pawl is positioned for engagement with the cam 61 and a retracted position shown in FIG. 5 in which the pawl is remote from the cam. The follower support 151 is held in its "follower ready" position by a suitable device, such as a detent 159, mounted on the support 53b and having an end receivable in a notch 165 in the follower support. Preferably, the detent 159 is pinned at 161 to the support 53b so that it can be manually or automatically pivoted out of the notch 165 to allow the follower support 151 to move down to its retracted position, preferably under the force of gravity. The pawl 99 is mounted on a pivot 167 on the follower support 151 for pivotal movement of the follower pawl relative to the support and to the cam 61.

A spring 177 biases the follower 99 (e.g., pawl) into contact with the cam surface 103. In the embodiment shown in FIGS. 3–5, the spring 177 comprises a torsion spring, although other springs, such as compression, extension or leaf springs, for example, are also contemplated as within the scope of the invention. The torsion spring 177 includes a first end 177a engaging a first pin 179 and a second end 177b engaging the follower 99 itself. The torsion spring 177 biases the follower 99 clockwise about pivot 167 to engage the cam 61. A stop 173 limits movement of the follower 99, such that when the toothless segment 111 of the cam 61 is adjacent the follower, the follower is spaced away from the cam surface 103 and cannot engage the cam (FIG. 3). This limit on the movement of the follower 99 allows the force measurement device 45 to measure the braking force on the cam 61 without the follower engaged, the importance of which will be discussed below. The normal force component imparted by the follower 99 on the cam surface 103 is dependent upon a distance D between axis C of the cam and a contact point P of the follower against the cam 61 (FIG. 4). Similarly, the braking force exerted by the follower 99 on the cam 61 as measured by the force measurement device 45 changes over time as the distance D changes. It should be noted that the force measurement device 45 may be placed at various locations for operable connection with the apparatus 21 without departing from the scope of the invention. For instance, a torque gage mounted on the shaft 57 of the apparatus 21 measuring a shaft torsional moment would provide an accurate dynamic force response.

Figure 6:
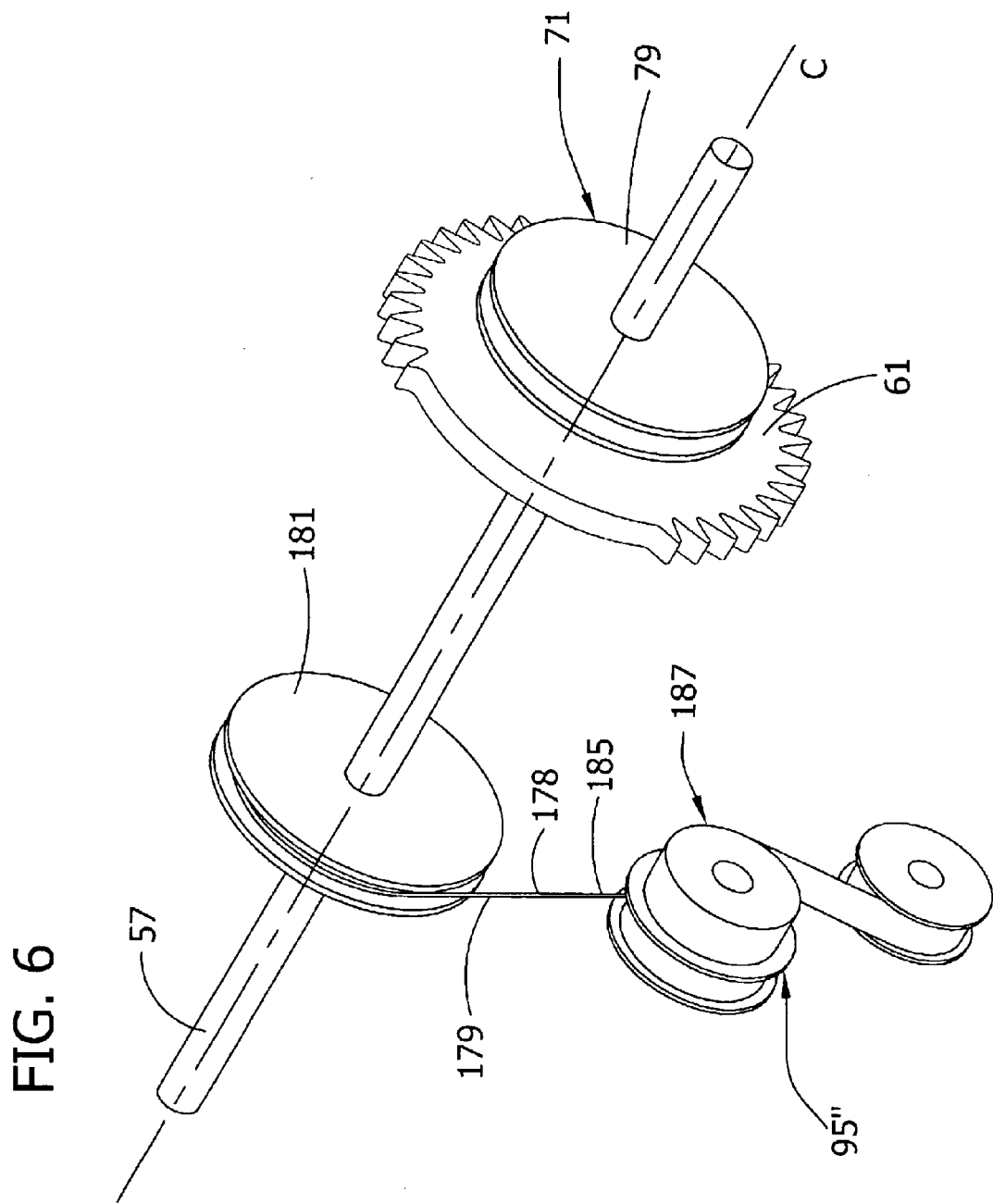
FIG. 6 is an isometric of the apparatus of FIG. 1 with portions removed to emphasize the interaction of particular elements.

Another braking device 95" of the present invention preferably further comprises a tensioning device, generally indicated 187, mounted on the primary support 53b and operatively connected to the cam 61 (FIGS. 2 and 6). In one embodiment, a braking cord 178 (wire, cable or other flexible line) operatively connects the cam 61 and the tensioning device 187. More specifically, a first end 179 of the cord 178 connects to a braking pulley 181 rotationally coupled to the cam 61 via the shaft 57. A second end 185 of the cord connects to the tensioning device 187. In the preferred embodiment, the braking force created by such a tensioning device 187 is substantially constant. Such tensioning devices are well known in the art. For example, the tensioning device 187 is preferably a Constant-Force Spring-Powered Return Reel, rated at 0.37 pounds, Model No. 61115A1, available from McMaster-Carr Supply of Chicago, Ill. Other tensioning devices, having different force ratings for instance, may also be used without departing from the scope of the present invention. In another configuration, the tensioning device comprises a mass (not shown) freely suspended by the braking cord 178 for creating a gravity-induced tension in the braking cord. The tensioning device 187 described above and creating a substantially constant braking force is designed to simulate a mass suspended from a cord.

In use, the apparatus 21 of the present invention operates to simulate dynamic force events. To perform such a simulation, the apparatus 21 is preferably manually set to the configuration shown in FIGS. 2 and 3, i.e., to a configuration where the follower support 151 is held in its "follower ready" position to position the pawl 99 for engagement with the cam 61, and the tensioning device 187 is properly connected to the pulley 181. With the follower pawl 99 in close proximity to the toothless segment 111 (FIG. 3), the tensile testing machine 25 is operated to move the crossbar 33 upward, causing the cam 61 and shaft 57 to rotate. The rotational speed profile of the cam 61 is determined by the speed of the crossbar 33, which can be controlled to provide the desired cam rotational speed profile. Once the crossbar 33 is set in motion, the remainder of the test process may be fully automated.

As the cam 61 rotates through its initial arc, the force required to rotate the cam is measured by the force measurement device 45 to provide a baseline force 197 (FIG. 7) based solely upon the braking force applied by the tensioning device 187, without braking force contributions from the follower 99 and cam, which are not yet engaged. After the toothless segment 111 rotates past the follower 99, the follower pawl contacts successive teeth 107 on the cam surface 103 (FIG. 4). As described above, the follower 99 is urged by spring 177 against the cam surface 103 and imparts a force against the surface. (Alternatively, the pawl 99 could be urged against the cam 61 by gravity.) As the cam 61 rotates, the normal component of this force increases as distance D increases and the follower 99 moves further from axis C along each tooth 107. As the contact point P of the pawl passes over the peak of each tooth 107, the normal force component on the cam 61 quickly drops as the pawl moves toward axis C and distance D decreases. As the pawl 99 passes over successive teeth 107 of the cam 61, the pattern of increasing and decreasing forces as measured by the force measurement device 45 creates a sawtooth pattern 199 in the measured braking force acting upon the cam 61 (e.g., FIG. 7). Following a complete revolution of the cam 61, a protuberance 201 on the cam engages the detent 159 and rotates it counterclockwise until the detent exits the notch 165, allowing the follower support 151 to pivot down under the force of gravity about pin 155 to disengage the follower 99 from the cam 61. Without the force of the follower 99 on the cam, the measured braking force returns to the baseline force 197 and data collection ends.

The present invention further comprises a method of dynamically calibrating multiple measured characteristics (e.g., force, displacement, speed control) of a testing machine simultaneously, such as a tensile testing machine 25, by collecting braking force measurements generally as described above. Before a testing machine can be properly calibrated according to the present invention, however, two other steps must occur. The steps include establishing a testing machine known to operate properly and creating a standard test based upon that testing machine. By combining these two steps with the method of calibrating, a calibration process is defined. The steps will now be described in detail with reference to a tensile testing machine 25, although they are generally useful when creating a calibration protocol for any testing machine.

First, one skilled in the art establishes that a particular tensile testing machine 25 is operating properly. For example, a tensile testing machine 25 recently maintained, statically calibrated and accurately performing peel tests with test samples may be classified as operating properly. Tensile testing machines 25 need not necessarily exhibit all three of these characteristics to operate properly, however; one skilled in the art may consider different or additional criteria, depending upon the specific tensile testing machine or test to be performed.

Figure 8:
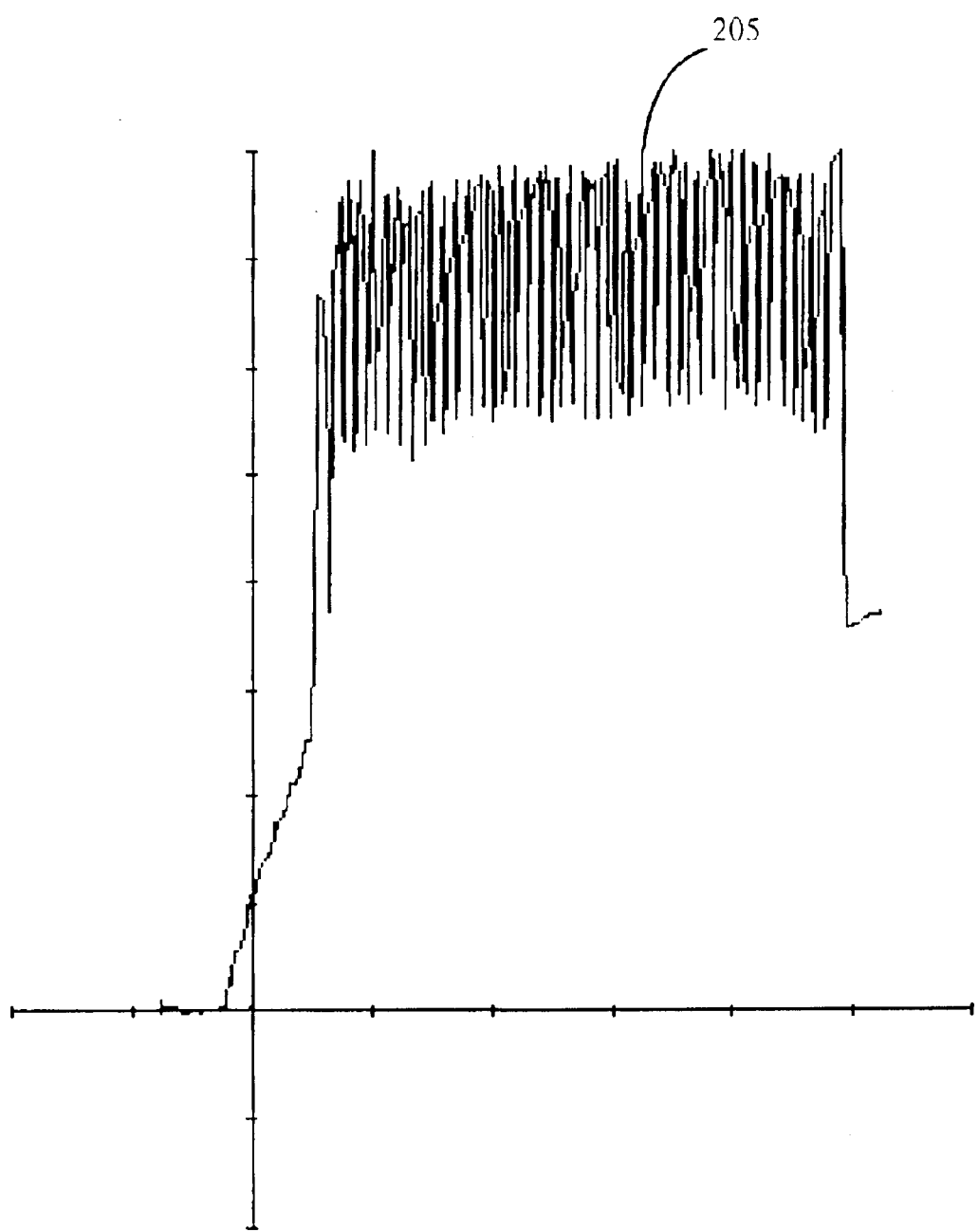
FIG. 8 is a plot of a standard dynamic force response, wherein the x-axis represents extension and the y-axis represents force.

Second, apparatus 21 of the present invention is mounted (installed) on the tensile testing machine 25 which has been established as operating properly. The tensile testing machine 25 then cycles through an entire test with the apparatus 21 as described above. The braking forces on the cam 61 are measured and collected over time to establish a standard dynamic force response 205 (FIG. 8). The response depicted in FIG. 8 is illustrative only, and is submitted as an example of such a standard. It should be readily apparent to one skilled in the art that altering the apparatus 21 or tensile testing machine 25 could alter the details of such a response, without departing from the scope of the invention. Once established, the standard dynamic force response 205 may then be utilized to calibrate other tensile testing machines 25, where the operational characteristics of the machines are unknown.

Third, now that the standard dynamic force response 205 is established, tensile testing machines 25 of unknown operational quality may be calibrated according to the standard. In one scenario, the tensile testing machine 25 of unknown operational quality may be the same machine used to develop the standard, but at a time remote from the standard establishing test, when the machine may or may not be operating properly (e.g., after sufficient time has passed or a large number of tests have occurred). In another scenario, the standard may be developed on a first tensile testing machine 25 and applied to a second tensile testing machine. In any event, the apparatus 21 is installed on the tensile testing machine 25 of unknown operational quality and performs a test identical to the one used to establish the standard dynamic force response 205. The braking force on the cam 61 is measured and collected over time to produce the simulated dynamic force response 115, rather than the standard dynamic force response 205. The simulated dynamic force response 115 is then compared to the standard dynamic force response 205 to calibrate the tensile testing machine 25.

Where a comparison of the simulated dynamic force response 115 and the standard dynamic force response 205 reveals that the two responses share substantially identical shapes and characteristics, the accuracy of the tensile testing machine 25 and the force measuring device 45 is confirmed. However, if the comparison reveals substantial 4 differences between the responses 115, 205, then the tensile testing machine 25 should be calibrated. In addition, the tensile testing machine 25 itself should undergo routine maintenance before retesting. In other words, the calibration method determines whether the tensile testing machine 25 of unknown operational quality is performing accurately by comparing the simulated dynamic force response of such machine with a standard dynamic force response produced by a tensile testing machine functioning properly. If the tensile testing machine 25 cannot emulate the standard response, then the machine is not operating properly.

When comparing the simulated dynamic force response 115 and the standard dynamic force response 205, any number of comparisons may be made to determine the performance of the tensile testing machine 25 of unknown operational quality. For instance, particular characteristics of the responses may be compared to calibrate the tensile testing machine 25. More specifically, the mean forces of the dynamic force responses 115, 205 may be compared to determine if the measured forces provided by the tensile testing machine 25 of unknown operational quality are similar in magnitude to those of the standard dynamic force response. Alternatively, the standard deviation of the force readings of the simulated dynamic force response 115 and the standard dynamic force response 205 may be compared to determine if the measured forces provided by the tensile testing machine 25 of unknown operational quality are grouped as tightly together as those of the standard dynamic force response. Finally, scatter plots of the force measurements (e.g., FIGS. 7 and 8) of the simulated dynamic force response 115 and the standard dynamic force response 205 may be compared to determine-if the measured forces of the tensile testing machine 25 of unknown operational quality vary over time in a manner substantially similar to those of the standard dynamic force response. Other statistical comparisons useful when comparing two sets of data may also be used to compare the simulated dynamic force response 115 and the standard dynamic force response 205 without departing from the scope of the present invention.

While the apparatus described above may include a cam and a follower, it will be understood that the present invention is not limited to this type of mechanism, and that other mechanisms may be used to simulate a dynamic force response. In general, apparatus 21 of this invention comprises a first body movable according to a specified speed profile and a second body biased into contact with a surface on the first body to impart a force against the surface. More generally, the first and second bodies need only move relative to one another, such that the second body may also be the moving body. A measurement device operatively connects to the first body (or moving body) to measure the dynamic force response on the first body as the first body moves according to the speed profile. The force varies according to the force of the second body on the first body and the friction between the surface and the second body as they move against one another. The apparatus preferably further comprises an additional braking device operatively connected to the first body to apply a braking force resisting movement of the first body. Such a braking force may be substantially constant, as produced by a constant tensioning device as set forth above.

In view of the above, it will be seen that the several objects of the invention are achieved and other advantageous results attained.

When introducing elements of the present invention or the preferred embodiment(s) thereof, the articles "a," "an," "the," and "said" are intended to mean that there are one or more of the elements. The terms "comprising," "including," and "having" are intended to be inclusive and mean that there may be additional elements other than the listed elements.

As various changes could be made in the above without departing from the scope of the invention, it is intended that all matter contained in the above description and shown in the accompanying drawings shall be interpreted as illustrative and not in a limiting sense.

What is claimed is:

1. Apparatus for simulating a dynamic force event in a force testing machine, said apparatus comprising:
    a cam rotatable about an axis according to a rotational speed profile;
    a braking device operatively connected to said cam for generating a braking force resisting rotation of the cam;
    a force measurement device for measuring the braking force on the cam as the cam rotates according to said rotational speed profile; and
    a mechanism connecting the cam to said force measurement device to permit the force measurement device to measure the braking force on the cam as the cam rotates according to said rotational speed profile.

2. Apparatus for simulating a dynamic force event in a force testing machine, said force testing machine having a movable force measurement device, said apparatus comprising:
    a cam rotatable about an axis according to a rotational speed profile;
    a drive device for rotating the cam in response to movement of the measurement device;
    a braking device operatively connected to said cam for generating a braking force resisting rotation of the cam; and
    a mechanism connecting the cam to said force measurement device whereby the force measurement device measures the braking force on the cam as the cam rotates according to said rotational speed profile.

3. A calibration device for use in calibrating a force testing machine, said force testing machine having a force measurement device, said calibration device comprising:
    apparatus for simulating a dynamic force event in the force testing machine, said apparatus being adapted for being removably mounted on said force testing machine, said apparatus comprising:
    a cam rotatable about an axis according to a rotational speed profile;
    a braking device operatively connected to said cam for generating a braking force resisting rotation of the cam; and
    a mechanism for connecting the cam to said force measurement device whereby the force measurement device is adapted to measure the braking force on the cam as the cam rotates according to said rotational speed profile.

4. Apparatus for simulating a dynamic force, said apparatus comprising:
    a first body;
    a second body biased into contact with a surface on said first body to impart a braking force against said surface, said first and second bodies being movable relative to one another according to a specified speed profile;
    a measurement device operatively connected to said first body to measure the braking force on said first body as the bodies move relative to one another according to said speed profile, said braking force varying according to the friction between said surface and said second body moving against one another; and
    a tensioning device operatively connected to said first body to apply an additional braking force resisting movement of said first body.

5. Apparatus as set forth in claim 4 wherein said additional braking force is substantially constant.

6. Apparatus as set forth in claim 4 further comprising a braking cord operatively connecting said first body and said tensioning device.

7. Apparatus as set forth in claim 4 wherein said tensioning device comprises a mass suspended by a braking cord for creating a gravity-controlled tension in said braking cord.

8. Apparatus for simulating a dynamic force, said apparatus comprising:
    a first body;
    a second body biased into contact with a surface on said first body to impart a braking force against said surface, said first and second bodies being movable relative to one another according to a specified speed profile; and
    a measurement device operatively connected to said first body to measure the braking force on said first body as the bodies move relative to one another according to said speed profile, said braking force varying according to the friction between said surface and said second body moving against one another.

9. Apparatus as set forth in claim 8 wherein said first body is adapted to rotate.

10. Apparatus as set forth in claim 8 further comprising a linear drive mechanism adapted for moving the measurement device along a linear path and a drive mechanism for rotating the first body in response to movement of the linear drive mechanism along said linear path.

11. Apparatus as set forth in claim 10 wherein said linear drive mechanism is incorporated in a tensile testing machine.

12. Apparatus as set forth in claim 11 wherein said measurement device comprises a load cell.

13. Apparatus for simulating a dynamic force event in a force testing machine, said force testing machine having a force measurement device, said apparatus comprising:

a cam rotatable about an axis according to a rotational speed profile;

a braking device operatively connected to said cam for generating a braking force resisting rotation of the cam; and a mechanism for connecting the cam to said force measurement device whereby the force measurement device is adapted to measure the braking force on the cam as the cam rotates according to said rotational speed profile.

14. Apparatus as set forth in claim 13 wherein said rotational speed profile varies over time.

15. Apparatus as set forth in claim 13 in combination with a tensile testing machine having a linear drive mechanism adapted for moving the force measurement device along a linear path, and a linear-to-rotary drive mechanism adapted for rotating the cam in response to movement of the measurement device along said linear path.

16. Apparatus as set forth in claim 15 wherein said linear-to-rotary drive mechanism includes a drive pulley rotationally coupled to said cam.

17. Apparatus as set forth in claim 13 wherein said rotational speed profile is substantially constant.

18. A combination of the apparatus set forth in claim 17 and said measurement device.

19. A combination of the apparatus set forth in claim 18 and a tensile testing machine attachable to said measurement device for moving said measurement device and controlling the rotation of said cam.

20. A combination of the apparatus set forth in claim 17 and a drive device for rotating the cam in response to movement of said measurement device.

21. Apparatus as set forth in claim 20 wherein said drive device includes a driving cord connected at one end to said measurement device and connected at an opposite end to a drive pulley rotationally coupled to said cam.

22. Apparatus as set forth in claim 13 wherein said braking device comprises a tensioning device operatively connected to said cam.

23. Apparatus as set forth in claim 22 wherein said tensioning device applies a substantially constant force.

24. Apparatus as set forth in claim 23 further comprising a braking cord operatively connecting said cam and said tensioning device.

25. Apparatus as set forth in claim 24 further comprising a braking pulley rotationally coupled to said cam, said braking cord having a first end connected to said braking pulley and a second end connected to said tensioning device, said braking cord operatively connecting said cam and said tensioning device.

26. Apparatus as set forth in claim 24 wherein said tensioning device comprises a mass suspended by the braking cord for creating a gravity-controlled tension in said braking cord.

27. Apparatus as set forth in claim 13 wherein said braking device comprises a follower biased into contact with a surface of the cam for imparting a variable force component of said braking force against said surface, said braking force varying according to the friction between said cam surface and said follower moving against one another.

28. Apparatus as set forth in claim 27 wherein said braking device further comprises a constant tensioning device operatively connected to said cam for imparting a constant force component of said braking force against said cam.

29. Apparatus as set forth in claim 27 further comprising a spring for biasing said follower into contact with said cam surface.

30. Apparatus as set forth in claim 29 wherein said spring comprises a torsion spring.

31. Apparatus as set forth in claim 29 wherein said variable force imparted by said follower on said cam surface is dependent upon the distance between the rotational axis of the cam and a point of follower contact with the cam, such that the braking force on said cam au measured by the measurement device changes over time according to said distance.

32. Apparatus as set forth in claim 27 wherein said cam surface is shaped to vary the braking force over time to simulate said dynamic force event.

33. Apparatus as set forth in claim 32 wherein said cam surface includes a segment having teeth and said follower comprises a pawl adapted to contact the teeth.

34. Apparatus as set forth in claim 33 wherein said teeth are of uniform size and evenly spaced along said cam surface.

35. Apparatus as set forth in claim 34 wherein said cam surface includes a toothless segment sized and shaped to remain free of contact with said follower.

\* \* \* \* \*

UNITED STATES PATENT AND TRADEMARK OFFICE
CERTIFICATE OF CORRECTION

| | |
|---|---|
| PATENT NO. | : 6,945,121 B2 |
| APPLICATION NO. | : 10/309836 |
| DATED | : September 20, 2005 |
| INVENTOR(S) | : Honer et al. |

It is certified that error appears in the above-identified patent and that said Letters Patent is hereby corrected as shown below:

On the title page item [73] Assignee: "Kimberly, Clark Worldwide, Inc." should read -- Kimberly-Clark Worldwide, Inc. --.

Column 8, Line 41: "substantial 4 differences" should read -- substantial differences --.

Signed and Sealed this

Twelfth Day of December, 2006

JON W. DUDAS
*Director of the United States Patent and Trademark Office*